(12) United States Patent  (10) Patent No.: US 9,033,955 B2
Singer  (45) Date of Patent: May 19, 2015

(54) DEVICE FOR TREATING PNEUMOTHORAX, TENSION PNEUMOTHORAX, PLEURAL EFFUSION, AND HEMOTHORAX IN NEONATES

(76) Inventor: Howard Singer, Schaumburg, IL (US)

( * ) Notice: Subject to any disclaimer, the term of this patent is extended or adjusted under 35 U.S.C. 154(b) by 519 days.

(21) Appl. No.: 12/388,251

(22) Filed: Feb. 18, 2009

(65) Prior Publication Data

US 2009/0227987 A1  Sep. 10, 2009

Related U.S. Application Data

(60) Provisional application No. 61/068,446, filed on Mar. 7, 2008.

(51) Int. Cl.
| | |
|---|---|
| *A61M 29/00* | (2006.01) |
| *A61M 25/06* | (2006.01) |
| *A61B 17/34* | (2006.01) |
| *A61M 1/04* | (2006.01) |
| *A61M 1/00* | (2006.01) |
| *A61M 37/00* | (2006.01) |

(Continued)

(52) U.S. Cl.
CPC ........ *A61M 25/0606* (2013.01); *A61B 17/3401* (2013.01); *A61M 1/04* (2013.01); *A61M 2025/0063* (2013.01); *A61M 2205/073* (2013.01); *A61M 2210/101* (2013.01); *A61M 2240/00* (2013.01)

(58) Field of Classification Search
CPC ....... A61M 29/00; A61M 1/00; A61M 37/00; A61B 19/00
USPC .......................................... 604/540, 317, 321
See application file for complete search history.

(56) References Cited

U.S. PATENT DOCUMENTS

| | | | |
|---|---|---|---|
| 2,154,968 | A | 4/1939 | Alkio |
| 3,385,300 | A | 5/1968 | Holter |

(Continued)

FOREIGN PATENT DOCUMENTS

| | | |
|---|---|---|
| CN | 2207183 Y | 9/1995 |
| CN | 2255274 Y | 6/1997 |

(Continued)

OTHER PUBLICATIONS

SL Samelson et al., "The Thoracic Vent. Clinical Experience with a New Device for Treating Simple Pneumothorax," Chest, 1991:100, pp. 880-882, American College of Chest Physicians, Northbrook, IL.

(Continued)

*Primary Examiner* — Tatyana Zalukaeva
*Assistant Examiner* — Ilya Treyger
(74) *Attorney, Agent, or Firm* — Ice Miller LLP

(57) ABSTRACT

A device for the treatment of pneumothorax especially in neonates, which facilitates the simple one-hand introduction of a catheter-sheathed stylet through the chest wall and which contains a one-way valve outside the chest for the stat evacuation of the intrathoracic air or fluid. The device is capable of secure fixation to the chest wall until deemed no longer needed at which point it is quickly removable. The thoracic cavity is entered by a stylet which is surrounded by a catheter, the catheter lumen continuous with that of a lumenized dome which communicates with at least one upper port and one-way valving. One port is configured to allow Luer-Lok suction in the event of pleural effusion or hemothorax.

14 Claims, 9 Drawing Sheets

(51) Int. Cl.
*A61B 19/00* (2006.01)
*A61M 25/00* (2006.01)

(56) References Cited

U.S. PATENT DOCUMENTS

| | | | |
|---|---|---|---|
| 3,459,189 A | 8/1969 | Alley et al. | |
| 3,613,684 A | 10/1971 | Sheridan | |
| 3,703,899 A | 11/1972 | Calinog | |
| 3,777,757 A | 12/1973 | Gray | |
| 4,036,231 A | 7/1977 | Dodge et al. | |
| 4,153,058 A | 5/1979 | Nehme | |
| 4,240,433 A | 12/1980 | Bordow | |
| 4,392,853 A | 7/1983 | Muto | |
| 4,447,235 A | 5/1984 | Clarke | |
| 4,519,796 A | 5/1985 | Russo | |
| 4,592,741 A | 6/1986 | Vincent | |
| 4,632,671 A | 12/1986 | Dalton | |
| 4,813,941 A | 3/1989 | Shea | |
| 5,045,077 A | 9/1991 | Blake, III | |
| 5,078,689 A | 1/1992 | Keller | |
| 5,100,376 A | 3/1992 | Blake, III | |
| 5,192,274 A * | 3/1993 | Bierman | 604/180 |
| 5,204,094 A | 4/1993 | Brandely et al. | |
| 5,344,410 A | 9/1994 | Kolkin et al. | |
| 5,370,899 A | 12/1994 | Conway et al. | |
| 5,419,776 A | 5/1995 | Baer | |
| 5,478,333 A | 12/1995 | Asherman, Jr. | |
| 5,509,909 A | 4/1996 | Moy | |
| 5,693,031 A | 12/1997 | Ryan et al. | |
| 5,725,506 A | 3/1998 | Freeman et al. | |
| 5,807,341 A | 9/1998 | Heim | |
| 5,865,807 A | 2/1999 | Blake, III | |
| 5,897,531 A | 4/1999 | Amirana | |
| 5,997,486 A | 12/1999 | Burek et al. | |
| 6,103,695 A | 8/2000 | Lane et al. | |
| 6,330,882 B1 | 12/2001 | French | |
| 6,517,519 B1 | 2/2003 | Rosen et al. | |
| 6,569,121 B1 | 5/2003 | Purow et al. | |
| 6,638,253 B2 | 10/2003 | Breznock | |
| 7,048,724 B2 | 5/2006 | Grossman et al. | |
| 7,135,010 B2 | 11/2006 | Buckman et al. | |
| 7,229,433 B2 | 6/2007 | Mullen | |
| 7,244,245 B2 | 7/2007 | Purow et al. | |
| 7,252,086 B2 * | 8/2007 | Tanaka | 128/200.26 |
| 7,326,197 B2 | 2/2008 | Breznock et al. | |
| 7,533,696 B2 | 5/2009 | Paul, Jr. | |
| 2002/0143294 A1 * | 10/2002 | Duchon et al. | 604/131 |
| 2002/0161353 A1 | 10/2002 | Kortelling | |

FOREIGN PATENT DOCUMENTS

| | | |
|---|---|---|
| CN | 2267816 Y | 11/1997 |
| CN | 2366112 Y | 3/2000 |
| CN | 2479979 Y | 3/2002 |
| CN | 2590585 Y | 12/2003 |
| CN | 2621686 Y | 6/2004 |
| CN | 2834560 Y | 11/2006 |
| GB | 2423933 A | 9/2006 |
| KR | 20010090908 Y | 10/2001 |
| WO | WO 96/16690 * | 11/1994 |

OTHER PUBLICATIONS

Michael H. Baumann et al., "Management of Spontaneous Pneumothorax: An American College of Chest Physicians Delphi Consensus Statement," Chest 2001:190, pp. 590 et seq., American College of Chest Physicians, Northbrook, IL.

M Henry et al., "BTS Guidelines for the Management of Spontaneous Pneumothorax," Thorax 2003:58, pp. 1139-1152.

Chien-Ming Liu et al., "Pigtail Tube Drainage in the Treatment of Spontaneous Pneumothorax," American Journal of Emergency Medicine 2003:21, pp. 241-244, Elsevier, Inc.

C.-H. Chen et al., "Pigtail catheter drainage for secondary spontaneous pneumothorax," Q J Med 2006:99, pp. 489-491, Oxford University Press.

Donald A. Lackey et al., "The management of tension pneumothorax in the neonate using the Heimlich flutter valve," Journal of Pediatrics 1974:84, pp. 438-440.

Irfan Serdar Arda et al., "Treatment of pneumothorax in newborns: Use of venous catheter versus chest tube," Pediatrics International 2002:44, pp. 78-82.

John G. Shutack et al., "A New Device for Diagnosis and Treatment of Neonatal Pneumothorax," Pediatrics 1979:63, pp. 252-255.

B. L. Duffy, "Neonatal Pneumothorax: A simple drainage device," Anaesthesia 1976:301, pp. 403-405, Blackwell Science, Oxford, UK.

C. W. Pollard, "A New Instrument for Inserting Intercostal Catheters," Australia New Zealand Journal of Surgery 1985:55, 507-509, Blackwell Scientific Publications (Australia) Pty Ltd., Carlton, Victoria.

* cited by examiner

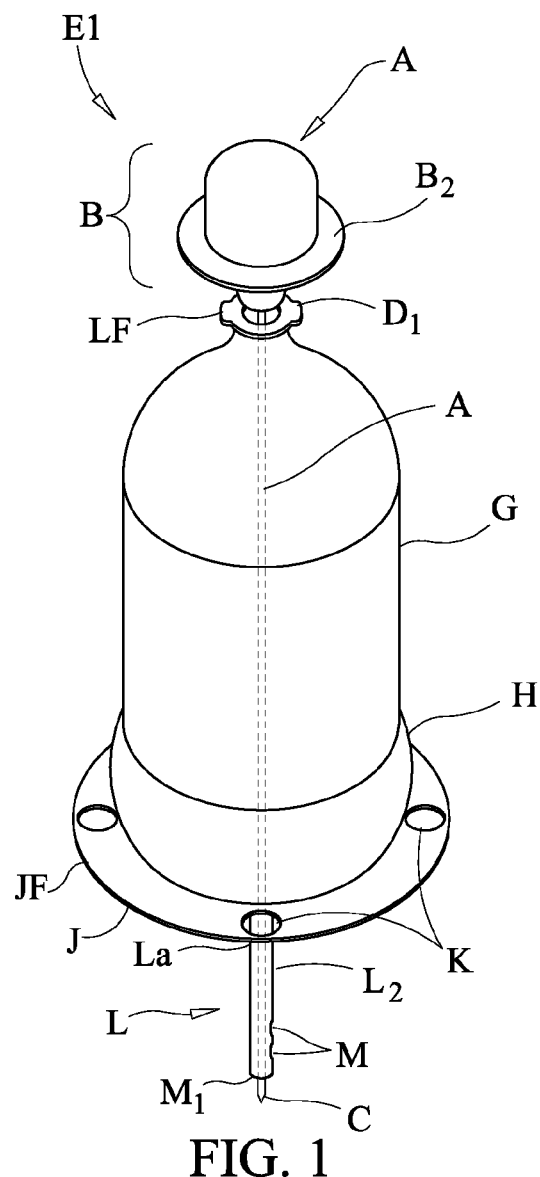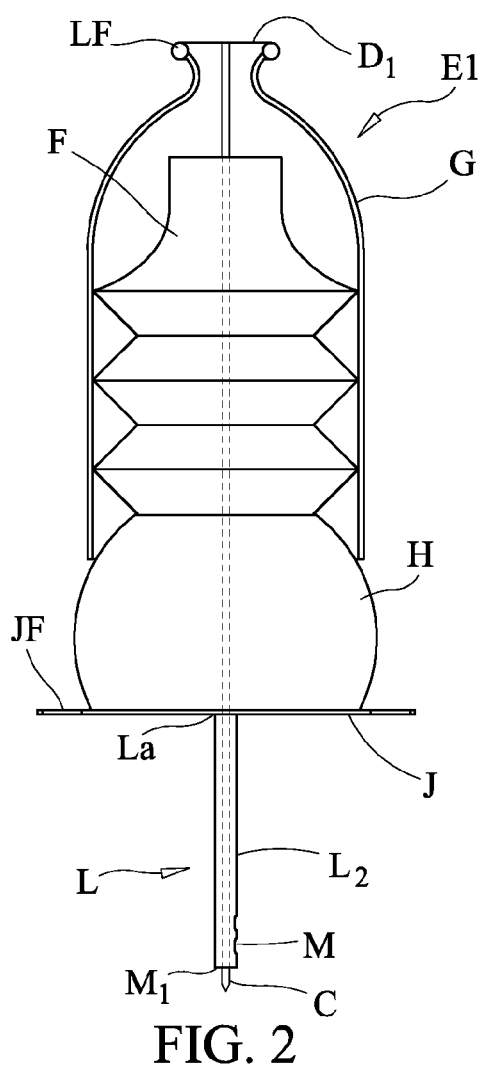
FIG. 1
FIG. 2

DEVICE FOR TREATING PNEUMOTHORAX, TENSION PNEUMOTHORAX, PLEURAL EFFUSION, AND HEMOTHORAX IN NEONATES

This application claims priority from U.S. Provisional Application Ser. No. 61/068,446, filed Mar. 7, 2008, which is hereby incorporated by reference.

FIELD OF THE INVENTION

The present invention relates to the emergency treatment of neonatal pneumothorax, tension pneumothorax, pleural effusion, and hemothorax.

BACKGROUND

The intrapulmonic air pressure exceeds the extrapulmonic intrapleural pressure under normal physiologic conditions, thus constituting the negative intrathoracic pressure deemed necessary for proper lung expansion. But when pleural air accumulates outside the lung, the negative pressure dynamics are disrupted, and the lung will begin to deflate unless emergency evacuation of pleural air is accomplished. Pneumothorax is usually spontaneous, but may follow trauma such as barotrauma from mechanical ventilation as applied to distressed neonates. Normally the outer epithelial lining of the lung, the visceral pleura, adheres to the inner epithelial lining of the chest wall, the parietal pleura, separated by only a potential space normally uninvaded by air as long as physiologic negative pressure dynamics keep the lungs inflated. Tension pneumothorax results from bronchopulmonary injury which acts as a one way valve permitting the abnormal egress of air into the pleural space, causing extrapulmonic air trapping which is aggravated by positive pressure ventilation or bagging. In distressed artificially ventilated neonates who suddenly worsen, life support trainees are mindful of the acronym DOPE which represents Displacement of the endotracheal tube, Obstruction, Pneumothorax, and Equipment failure. A quick inventory of breath sounds and mechanical equipment can rule out displacement, obstruction, and equipment failure, but pneumothorax must be suspected when an infant suddenly deteriorates after initially responding to positive pressure ventilation, manifests unilateral decrease in chest wall expansion, altered intensity or pitch of breath sounds, and increased resistance to manual ventilation. One may find mediastinal shift, decreased breath sounds on the involved side, homolaterally distended neck veins, contralateral tracheal deviation. Pneumothorax and especially tension pneumothorax are life threatening emergencies which demand prompt intervention. Prior to chest tube or catheter placement, noninvasive treatment includes oxygen and parenteral volume expanders, and one should check the blood glucose and oxygen saturation.

If time permits, one can order a chest film with crosstable lateral view. Radiographically one may see a thin sharp white line representing pleura, absent parenchymovascular markings beyond the pleura, air beyond the pleura represented by a dark lucency, increased lucency over one lung field, a deep sulcus sign at the lateral costophrenic angle in the case of a basilar pneumothorax, increased sharpness of the mediastinal border in the case of a medial pneumothorax, anterior lucency on the crosstable lateral with pneumomediastinum, or depressed hemidiaphragm on the homolateral side with tension pneumothorax. If one suspects pneumothorax and there is insufficient time to obtain an Xray, chest transillumination may be attempted for confirmation. With or without an Xray, if clinical suspicion persists, one locates the 2nd intercostal space in the midclavicular line, or the 5th intercostal space in the anterior axillary line, bearing in mind that the nipple is at the 4th intercostal space. Currently utilized procedures typically include prepping the skin with povidone or chlorhexidine, infiltrating intradermal lidocaine, inserting a catheter-covered needle through the chest wall, withdrawing the needle, and connecting the indwelling intrapleural catheter to a one-way valve or waterseal.

Pneumothorax occurs in 2% of all neonates, or about 40,000 of the nearly two million births annually in the US, 19% of all neonates with respiratory distress syndrome (RDS), at least 20% of RDS neonates treated with continuous positive airway pressure, and 36% of neonates with meconium aspiration. In addition to RDS and meconium aspiration, risk factors for neonatal pneumothorax include transient tachypnea of the newborn, perinatal asphyxia, cardiopulmonary resuscitation with mechanical ventilation, and elective cesarian section. Among normal term infants delivered electively by cesarian section, pneumothorax occurs at a rate of 2.9/1000 in such babies (*J Ped* 2007; 150:252). Elective cesarian section is an obstetrical modality which is gaining in popularity in both the US and UK. Cesarian deliveries overall approach a half million per year in the US, most of them elective. Aspirated meconium may act as a one-way valve and result in tension pneumothorax.

Pneumothorax is a frequent concomitant of these conditions and must be recognized and treated promptly. Neonatal pneumothorax likewise requires immediate recognition and treatment, hopefully minimizing instrumentation and trauma. Nonsurgical management includes endotracheal visualization and suction of meconium as needed, oxygen, circulatory volume expansion, management of associated infection and hypoglycemia, Narcan if indicated, and other appropriate supportive measures.

Pneumothorax in all age groups is a medical emergency, and particularly so in the neonate in whom clinical deterioration typically occurs at an alarming rate. Tension pneumothorax rapidly worsens with mechanical ventilation, as its one-way valve and malignant air trapping quickly result in mediastinal shift and diminished venous return which impair diastolic filling. Ultimately the plummeting cardiorespiratory function will be fatal without prompt intervention, and the urgency inherent in pneumothorax management requires that any treatment device not entail any undue expenditure of time summoning extra personnel and equipment.

There is an ongoing need for a compact rescue device that can be quickly and safely implemented by relatively inexperienced personnel for the immediate treatment of pneumothorax, particularly neonatal pneumothorax and tension pneumothorax, in situations involving respiratory distress, meconium aspiration, perinatal asphyxia, transient tachypnea of the newborn, or any scenario which includes artificial ventilation and bagging in the delivery room or neonatal intensive care unit.

SUMMARY

The primary object of the invention is to provide a device that can be employed by first responders including personnel who are capable of recognizing neonatal pneumothorax, and who therefore are in a position to rescue a neonate as well as older patients before the onset of dire sequelae such as hypoxia, progressive cardiopulmonary collapse, and death.

Another object is to avail first responders a device for stat use at scenes outside the hospital and aboard ambulances, which will not only relieve the pneumothorax but will allow pulmonary expansion and potentially definitive treatment as well.

Another object is to furnish personnel of limited experience in emergency rooms, delivery, and neonatal units with a device which is easily and quickly mastered and can be readily utilized when patients appear in respiratory distress as result of pneumothorax.

Another object is to provide a device which is safe to the extent that it will not cause significant damage, or impart iatrogenic pneumothorax by its use should the diagnosis be incorrect. This is in contrast to the current conventional approach with angiocatheters or pigtail catheter devices, which invade the pleural space thereby disrupting the normal negative intrathoracic pressure, do not provide the immediacy of one-way valves to preclude entry of outside air, and therefore could result in an iatrogenic pneumothorax if one did not pre-exist. The proposed device has one-way valving which precludes outside air entry, and its catheter is comprised of resilient material with longitudinal ribbing which resists kinking thereby resisting iatrogenic tension pneumothorax from equipment failure, and is radiopaque to facilitate radiographic identification after placement. Its stylet imparts a smaller entry wound than would larger-bore trocars, cannulae, or needles, noting also that a needle or cannula could core out and intrapleurally deposit an epithelial plug.

Another object is to preclude entry of contaminants into the pleural space of not only outside air, but also bacteria, chemical and radiologic substances, by virtue of its one-way valve.

Another object is to design a pneumothorax treatment device that is created with unified integral major components with regard to its one-piece lumenized dome, discoid base, and catheter, therefore is resistant to unintended separation or breakage of component parts, or anomalous assembly thereof.

Another object is to create a pneumothorax treatment device that is compact and occupies minimal storage space, does not require extra storage space for ancillary equipment, can be economically packaged, shipped, and stored, also is easily carried in large quantity.

Another object is to make a pneumothorax treatment device that can be readily and securely affixed to the chest wall without risking untimely separation or cutaneous damage from acrylic adhesives.

Another object is to produce a device wherein the lumen is protected by said disc and dome, thereby precluding kinking with obstruction at that level during transport or handling and thus precluding iatrogenic tension pneumothorax; wherein the catheter lumen is protected because said catheter is rigidified by an indwelling stylet and shielded by protective outer cuffing during shipping and storage; and wherein the risk of intrapleural kinking is obviated by quality manufacture with resilient materials and longitudinal ribbing of the catheter.

Another object is to develop a pneumothorax treatment device that, when upsized in multiple catheter and stylet lengths for patients beyond the neonatal period, would be well suited for mass casualties because of minimal storage space requirements and portability, easy implementation, definitive provision of relief, and valving that precludes entry of outside contaminants.

Another object is to provide a pneumothorax device that includes a specific connection for suction of pleural effusion or hemothorax via a secure Luer Lok fitting.

Another object is to provide a pneumothorax device that utilizes the stylet from a spinal (LP) needle, thereby minimizing trauma with its absence of a lumen. Unlike needles or cannulae, a stylet is nonlumenized and thus cannot core out an epithelial plug during insertion and risk depositing the plug intrapleurally with the risk of inflammatory sequelae. In preferred embodiments, said stylet is slidably derived from a spinal or LP needle, is therefore of smaller bore than the corresponding needle, thus imparts a smaller entry wound than would larger-bore needles, cannulae, and trocars.

Another object is to overcome shortfalls of a crowded art, which individually and collectively failed to recognize the advantages of a simple neonatal pneumothorax device wherein the whole is functionally greater than the sum of its parts, and failed to implement such a device which combines features and advantages in the manner presented by embodiments of the proposed device.

One aspect of the invention is a device for treating pneumothorax, pleural effusion or hemothorax, said device having a catheter with a proximal opening and distal opening, a rigid body with a port in communication with the proximal opening, and an aligned upper port, such that the device may be gripped with one hand, a one-way valve that allows egress of gases from the lower port and prevents ingress of gases, a removable sharp-pointed instrument with a shaft extending from the upper port through the catheter and extending a distance past the distal end, where the operator may use the device to penetrate the sharp pointed instrument through a chest wall into the intrapleural space while gripping the device with one hand.

In a further embodiment, the sharp pointed instrument may have a hub with a hub annulus, such that the sharp-pointed instrument may be removed by raising the hub annulus with one or two fingers while continuing to grip the body with fingers of the same hand. The upper port may be fitted with a Luer-lok or other suction device to allow for rapid liquid removal.

In one embodiment of this aspect of the invention, the one-way valve may be contained inside the body, configured to allow air or fluids to exit from the lower port through the upper port. The one-way valve may be a duckbill valve having an open end in communication with the lower port, and a closable end that opens in response to air or fluid pressure from the open end. The closable end of the duckbill valve may sealingly accommodate the shaft of the stylet in this embodiment.

In this aspect of the invention, the body may have a flat discoid surface around the lower port, and an intersecting dome, where the dome permits egress of air or fluids from the lower port to the one-way valve and the upper port. In this embodiment, the discoid surface, dome, and catheter may be of one-piece construction, and may be radiopaque. The discoid surface may comprise an outer ring extending from the intersection of the dome and discoid surface, and this outer ring has fenestrations to allow suturing of the device to the patient.

The device according to this aspect may also comprise a side port disposed on the base with the one-way valve disposed thereon, so that gases may exit through the side port without allowing ingress of gases through the side port. In this embodiment, the upper port may have an elastomer cap that sealingly accommodates the shaft of the sharp-pointed instrument without allowing gases to enter or exit. This elastomer cap may be removed to allow a syringe or suction device to be installed for liquid removal. In this embodiment with the side port, the device may also have a three-way stopcock separating the upper port, lower port, and side port. In one stopcock position, the upper and lower port are in communication and the stopcock accommodates the shaft of the sharp-pointed instrument. In a second position, the lower and side ports are in communication to allow gases to exit. In a third position, the upper and lower ports are in communication to allow liquid removal through the upper port.

In further refinements of this aspect of the invention, the catheter has a length suitable for penetration of a neonate's chest cavity. The catheter may have one or more apertures along its length, and it may have ribs along its length. The sharp-pointed instrument according to this aspect may be an eighteen gauge stylet.

Another aspect of the present invention is a unitary device for treating pneumothorax, pleural effusion, or hemothorax in neonates, employing a hollow body, a catheter connected to the body, a removable stylet sealingly disposed in the catheter, the stylet and catheter configured to penetrate the intrapleural space of a neonate, a one-way valve attached to the body to allow one way expulsion of gases after penetration, and a port that allows a syringe or suction device for fluid removal to be attached, configured so that that the stylet and catheter may be inserted into an intrapleural space, and subsequently the stylet removed using fingers of one hand.

A device according to this aspect may have a body less than 5 centimeters in width, and the body and catheter are of one-piece construction. A device according to this aspect may have a discoid surface on the body that is suturable to the patient's skin. In this aspect, gases may be released through the one-way valve immediately after the stylet is removed.

BRIEF DESCRIPTION OF THE DRAWINGS

The invention can be better understood with reference to the aforementioned and following drawings and description. In the drawings:

FIG. 1 is an isometric view of device E1, an embodiment in accordance with the present invention.

FIG. 2 is an isometric view of E1.

DETAILED DESCRIPTION

Figure 3:
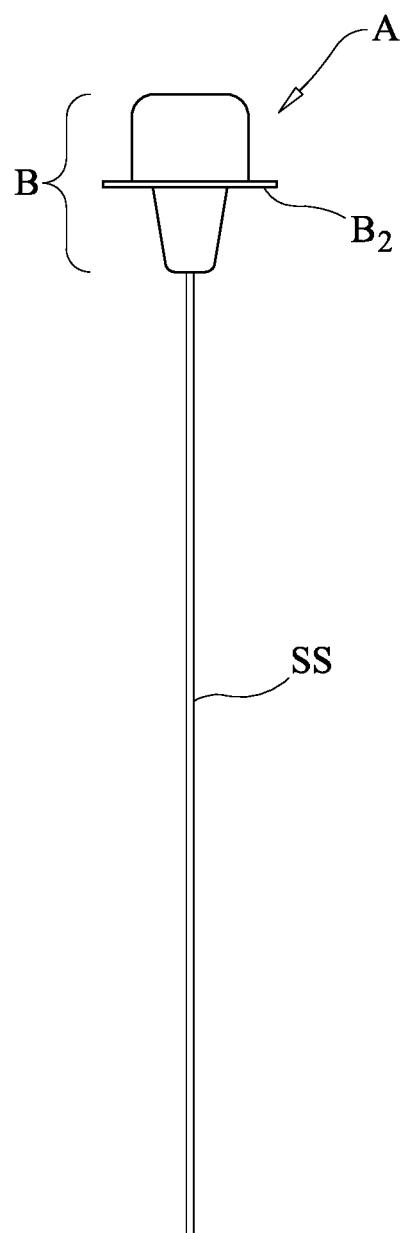
FIG. 3 is an exploded view of a stylet in accordance with embodiments of the present invention.

Described herein are embodiments of the proposed device that are intended primarily for the emergency treatment of neonatal pneumothorax, hemothorax, and pleural effusion, in a safe unified compact design readily mastered by first responders including those with limited clinical experience. Its catheter is connected to a discoid base and lumenized dome which communicate with ports and valving above skin level. One such port features an accordion duckbill escape valve for one way evacuation of intrapleural air, and a separate port employs a Luer Lok receptacle capable of connecting to a syringe or suction tubing in the event of the need to evacuate a pleural effusion or hemothorax. The upper port in two embodiments admits the stylet through a tethered twistoff cap comprised of elastomer or similar material which maintains its airtight seal thereby precluding air re-entry upon stylet removal, also providing seating for the stylet hub. Embodiment E1 requires no cap, as said duckbill valve is positioned vertically atop the dome surrounded by a clear sleeve. The upper port of said sleeve accommodates stylet entry and provides seating for the stylet hub. At the base of the dome is a disc with marginal fenestrations for connection to sutures for secure chest wall placement. All embodiments possess a lumenized dome, fenestrated flat discoid base, intrapleural catheter with distal side orifices, an accordion duckbill oneway valve, a Luer Lok fitting allowing for mechanical fluid suction via the upper port, said upper port providing entry for a stylet which slidably fits within a catheter, the sharp tip of said stylet protruding at least 0.2 cm beyond catheter's distal orifice. The overall ergonomic design favors easy grasp with thumb on one side of the dome, fourth and fifth fingertips on the opposite side of the dome, and simultaneous placement of index and third fingertips atop the hub of the stylet, allowing quick and simple introduction of the device. Subsequent to verified placement, said stylet may then be lifted out of the unit with index and third fingertips astride the stylet hub. Stylet hub has an annulus to facilitate stylet removal after placement. Proper selection of the site of introduction, skin prep, and local lidocaine infiltration will normally precede such introduction, but in an acute emergency, relief of pneumothorax can be achieved in seconds, followed by confirmation with auscultation, pulse oximetry, and radiographic identification of catheter placement. Other embodiments include scaled-up versions for use in toddlers, preschoolers, school-age children, adolescents, and adults.

FIG. 1 shows an embodiment E1 of the proposed device as assembled and ready for use. As shown, embodiment E1 comprises a stylet A entering an upper port with Luer Lok fitting D1, thence through accordion-duckbill valve F (not shown in FIG. 1), said valve surrounded by clear sleeve G, both sleeve G & valve F positioned vertically and contiguous with lumenized dome H and catheter L. The clear sleeve G and dome H form a rigid body, which may be 5 cm or less in width so that the body may be gripped with fingers of one hand. Stylet A is slidably and sealably surrounded by catheter L. FIG. 1 shows stylet hub B resting atop upper port D1, and sharp stylet tip C protruding through distal orifice M1 of catheter L. Asymmetrically placed side orifices M are shown on tube L2 of distal catheter L, also discoid base J with fenestrations K; see FIG. 12 for preferred suturing of E1 to patient's chest wall.

FIG. 2 shows a cutaway view of embodiment E1 of the proposed device. In this view, accordion duckbill valve F atop lumenized dome H can be seen.

FIG. 3 shows stylet A comprising solid stainless steel in a cylindrical shaft SS which tapers to a sharp distal point or tip C that may be used to penetrate a patient's thoracic skin, connective tissue, and muscle, and enter the intrathoracic pleural space so as to allow placement of catheter L to evacuate air or fluid. The sharp distal point or tip C of said stylet protrudes at least 0.2 cm beyond the distal end of the catheter L to enable penetration of patient's chest wall and entry into patient's pleural space. The shaft SS of said stylet A resides within and is covered by said discoid base and dome until the stylet is manually withdrawn and removed from the device. While a needle may be used, a solid bore stylet is preferred because the stylet has no lumen and therefore will not core out an epithelial plug during insertion, and then deposit said plug in the pleural space with the risk of pleuritic sequelae. An eighteen gauge stylet is preferred over a spinal needle because the stylet is of smaller bore than its corresponding needle, and therefore imparts less trauma to the patient upon penetration through the chest wall. The radiopacity of the stylet A is assured by its metal composition. Catheter L is likewise radiopaque by virtue of its radiodense materials, thereby providing a means of radiographically identifying the path, placement, and position of the catheter subsequent to insertion in the patient's thoracic cavity.

Stylet hub B has an annulus B2 for facilitating removal of the stylet A by the 2nd & 3rd fingertips of operator's hand upon successful intrapleural placement of the device. Said annulus is disposed around the inferior portion of stylet hub, the hub seated atop upper port D1 in embodiment E1 (see FIG. 1). In embodiments E2 and E3, the stylet hub is seated atop elastomer cap D2a. See FIGS. 5 & 8.

Figure 4:
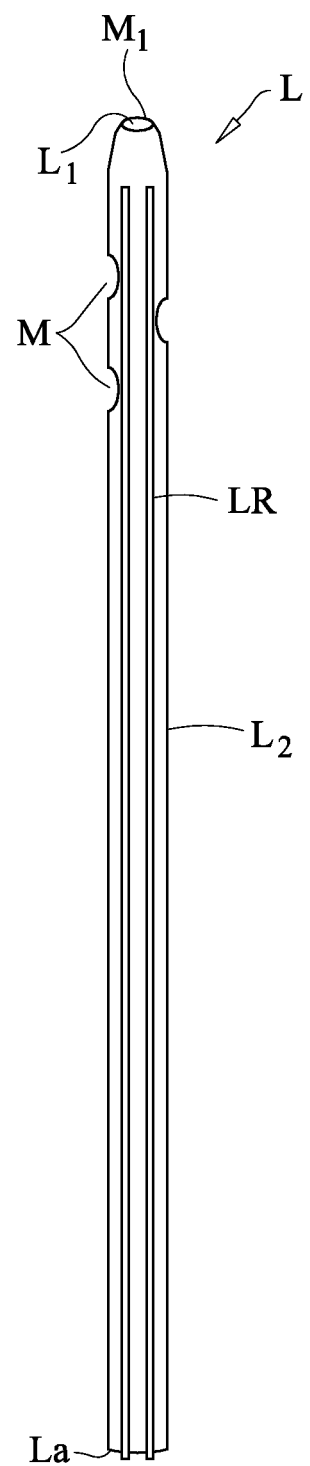
FIG. 4 is an exploded view of a catheter in accordance with embodiments of the present invention.

FIG. 4 shows an exploded view of catheter L, which consists of a hollow elongated tube L2 with a hub La on its proximal end. Tube L2 consists of currently available medical grade highly flexible and resilient radiopaque tubing rendered kink resistant by virtue of its longitudinal ribbing LR, and has one or more distal sidewall orifices M and an end orifice M1. M1 designates the orifice or opening at said catheter's distal or intrathoracic end, and M denotes the sidewall orifices which extend through the wall of tube L2 near its distal, intrathoracic end. Catheter hub La is cylindrical with a lumen continuous with that of lumenized dome H and valve F (see FIG. 2), said hub La of same intraluminal diameter as that of tube L2. Catheter hub La is comprised of the same material as tube L2, dome H, and discoid base J (shown on FIGS. 1, 5, and 8), all of which are cast as a one-piece unit. The catheter L is intended for venting trapped intrathoracic air or fluid to said valve via said discoid base J and said dome, so as to enable the one-way expulsion of the trapped air. The tube L2 has a lumen L1 that is configured to snugly engage the shaft of stylet A, a distal tube end M1 allowing protrusion of the sharp tip C of stylet A so as to enable penetration of said chest wall and entry into said thoracic cavity, a proximal tube end fused and continuous with said lumenized dome H to enable the conduction of said trapped air or fluid to said one-way valve for air expulsion and/or to the Luer Lok connection to a syringe or tubing for mechanical fluid suction, and a length of said catheter comprising the portion between proximal and distal ends of the tube. Radiopacity is achieved by virtue of radiodense material in catheter L, dome H, & discoid base J. Catheter L may have one or more side orifices M in the distal sidewall to permit additional portal of egress for trapped air and fluid from said intrapleural space. Said catheter L is radiopaque to enable radiographic identification and verification of its path and position relative to the intrapleural space. Identifying catheters by their radiopacity is well known to those reasonably skilled in radiographic interpretation, including clinicians of reasonable competence and experience. Said catheter is rendered kink resistant by virtue of resilient materials as well as longitudinal ribbing LR, and is resistant to separation from the discoid base and dome by virtue of the one piece manufacture of said catheter, discoid base, and dome.

Figure 5:
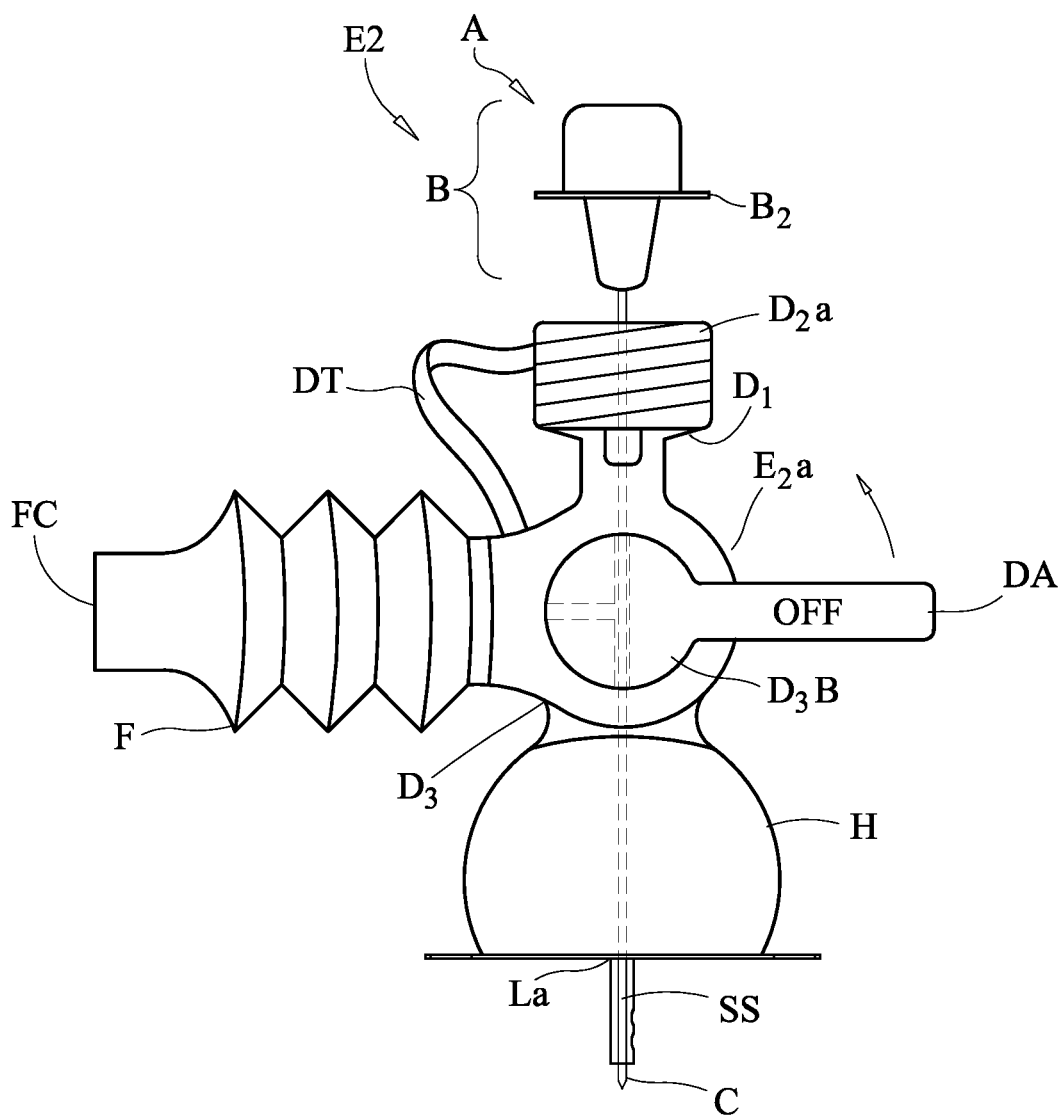
FIG. 5 is an isometric view of a device E2, an embodiment in accordance with the present invention.

FIG. 5 shows embodiment E2 of the device as assembled and ready for use. The upper body of E2 is labelled E2A, containing upper port D1, 3-way stopcock D3b, and side valveport D3. As shown, E2 comprises a stylet A entering the upper body U through an upper port D1, then through a channel bored in a 3-way stopcock D3b, wherein the stylet courses through said upper body thence through said dome, thence through the catheter, the catheter, upper port, and 3-way stopcock aligned to allow the stylet to pass through. The upper port is covered by a tethered elastomer twistoff cap D2a which sealingly surrounds the stylet B before the stylet is removed, and which prevents ingress of air when the stylet is removed. The cap is removable to expose a Luer Lok fitting around upper port D1, which allows the operator to connect with a syringe or other suction device in the event of pleural effusion or hemothorax. The cap D2a is tethered to the device by tether DT to preclude cap loss.

Like the device E1, the device E2 may be used to penetrate the thoracic cavity with one hand, two fingers holding the stylet hub, and two or three fingers gripping the body. The stopcock in this position (with toggle arm DA pointed to the right) is open to the upper port, the lumenized dome, and side valveport D3. When the stylet is removed, gases from the catheter pass through the lumenized dome, through the stopcock, and through the side valveport D3. However, elastomer cap D2a prevents ingress or egress of air through upper port D1, and accordion duckbill valve F prevents ingress of air through side valveport D3.

Said stopcock provides a means of selecting in a failsafe manner which port is to be closed, and which is to be opened. When the toggle arm DA is pointed upward (one quarter turn from the original position) stopcock D3b is closed to upper port D1, preventing inrush of outside air and thereby allowing the safe removal of the elastomer cap and attachment to suction. In this position, the stopcock D3b is open to the lumenized dome and catheter and to the side valveport to allow egress of trapped air, but not upper port D. If toggle arm DA of stopcock in this figure is rotated to the left another quarter turn toward valveport D3, the stopcock is open to the upper port D1 and to the lumenized dome and catheter, but is closed to the side valveport D3 and accordion duckbill valve F. This position allows suction of liquids via the upper port after the operator has removed the elastomer cap and installed a syringe or suction device, and thus permits fluid removal from the pleural space. Thus, in embodiment E2, if the operator seeks to withdraw pleural fluid or blood, toggle arm DA is rotated first upward to close upper port D1 to permit safe removal of twistoff cap D2a, then syringe is attached, then arm DA is rotated leftward to seal side valveport D3 thereby closing said valve to enable suction via Luer Lok fitting LF on upper port D1.

Figure 5A:
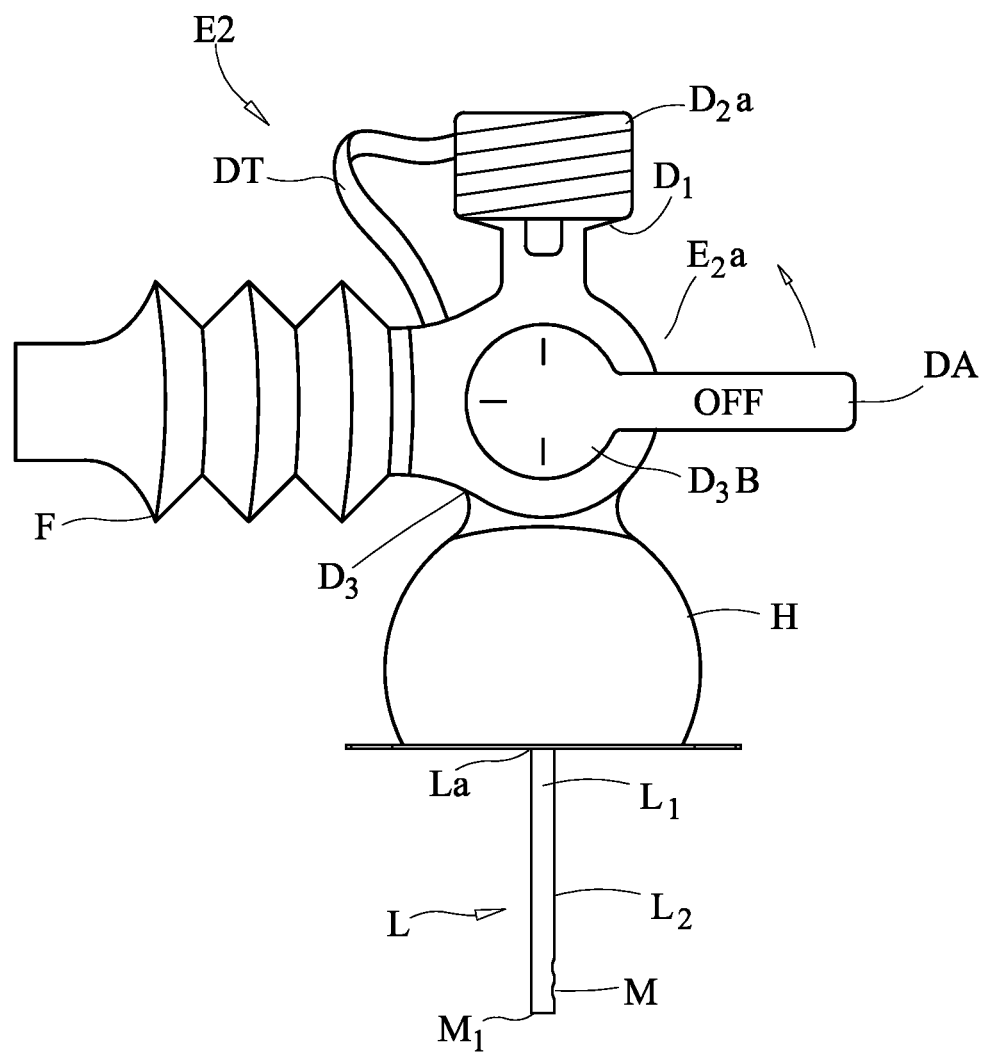
FIG. 5a is an isometric view of E2 with the stylet removed.

FIG. 5a shows embodiment E2 of the proposed device is shown in isometric view with the stylet removed.

Figure 6:
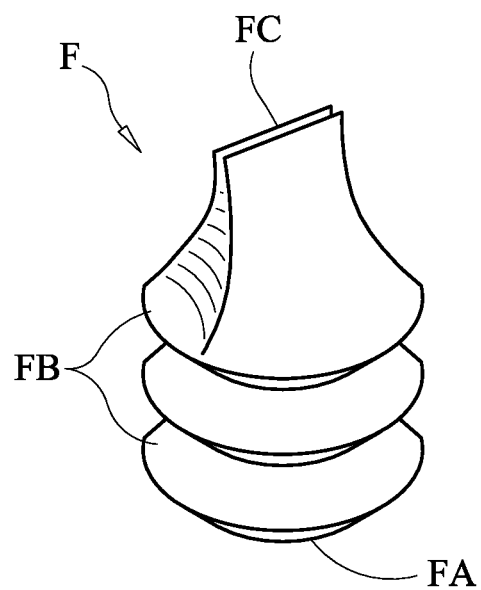
FIG. 6 is an exploded view of accordion duckbill one-way valve in accordance with embodiments of the present invention.

FIG. 6 shows an exploded view of valve F, which consists of a one way accordion shafted duckbill valve permitting the egress of trapped air, but prohibiting the entry of outside gases and contaminants, in a flexible design to allow expansion and contraction with respiratory phases and the rise and fall of intrathoracic pressure generated within the thoracic cavity. When not in use, the lips FC of the duckbill valve remain pressed together as a function of the valve's natural elasticity. The duckbill is designed to open sufficiently to allow egress and expulsion of trapped air conducted to the opening FA by catheter L and dome H upon contraction of the thoracic cavity during exhalation. The force of expelled air separates the lips FC of the valve F, thereby permitting the air to exit via the valve's distal end, but the lips coapt snugly after egress and expulsion to prohibit entry of outside gases and chemicals during the inspiratory phase and the increased intrathoracic negative pressure generated within the thoracic cavity during inhalation. Duckbill valve F is comprised of flexible resilient material similar to that of the catheter L, discoid base J, and dome H. The valve proximal end FA is contiguous with side valveport D3 in E2 (see FIGS. 5 and 5A) and E3 (see FIGS. 8 and 8A), and is contiguous with the top of lumenized dome H in E1. Accordion-like pleats FB expand and contract with rise and fall of intrathoracic pressure. Entrapped intrapleural air passes finally through resilient valve lips FC which part to allow expulsion of air, but which remain coapted in resting state. The lips FC further are capable of remaining sealingly coapted around the shaft SS of stylet B in embodiment E1 (see FIG. 2).

Figure 7:
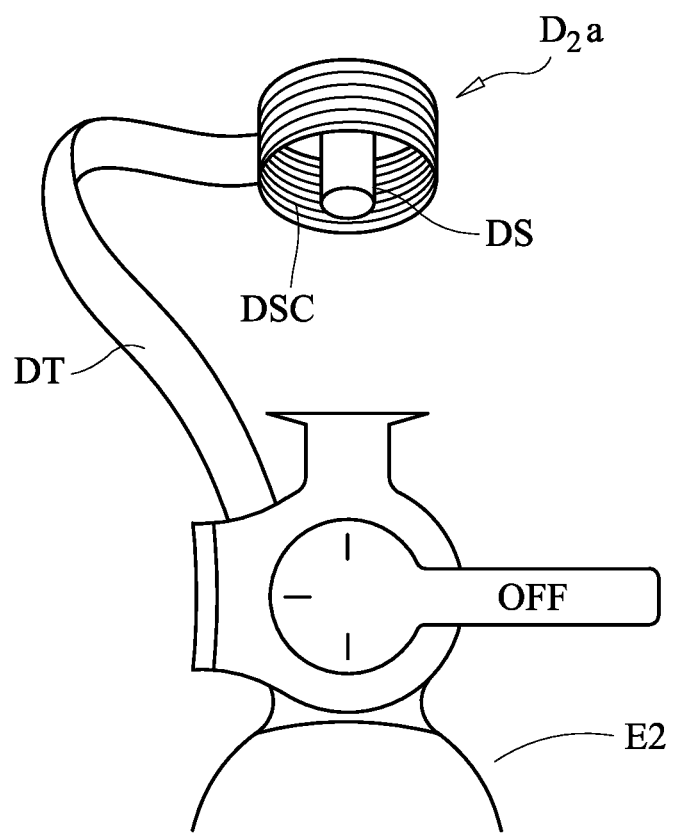
FIG. 7 is an exploded view of an airtight tethered elastomer cap in accordance with embodiments of the present invention that sealingly admits a stylet, but remains airtight upon stylet removal.

FIG. 7 shows an exploded view of tethered twistoff elastomer cap D2a in embodiments E2 and E3 (note that embodiment E3 does not use the stopcock shown in FIG. 7) which covers upper port D1, said cap permitting airtight stylet entry and removal. Cap D2a is removable to expose Luer Lok fitting LF for fluid suction. Rotatable arm DA of stopcock D3b prevents air entry after said cap removal prior to syringe attachment for suction. The cap has screw threading DSC on its interior walls which promote an airtight seal with matching screw threading on the body, when secured onto upper port D1. The cap has a descending stopper DS on its lower portion of said cap that fits inside opening of upper port D1. The shaft SS of stylet A is sealingly contained in this stopper DS when the stylet is seated. A tethered connection DT prevents cap loss following the cap's removal for suction.

Figure 8:
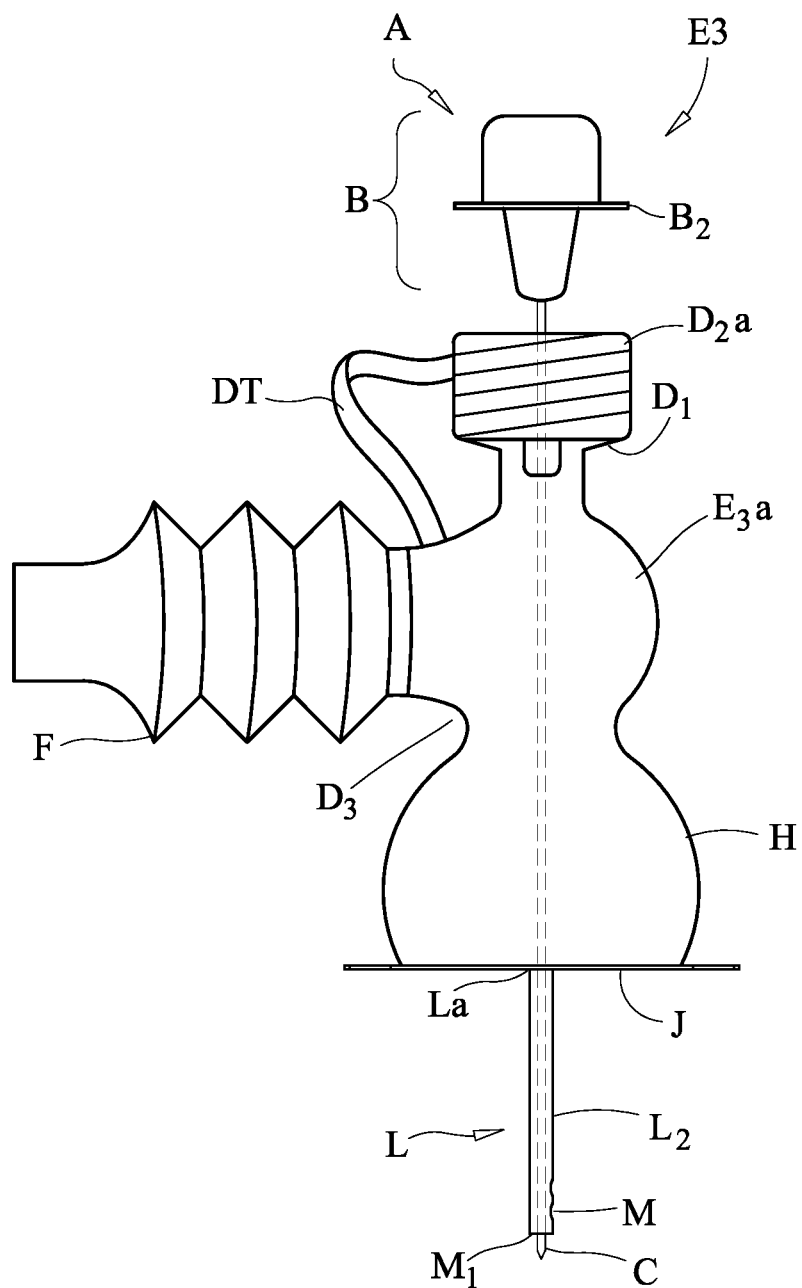
FIG. 8 is an isometric view of a device E3, an embodiment according to the present invention.
Figure 12:
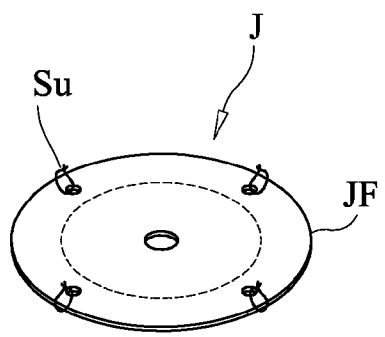
FIG. 12 is an exploded view of a discoid base in accordance with embodiments of the present invention, showing interrupted sutures through peripheral fenestrations for anchoring the device securely.

FIG. 8 shows embodiment E3 of the proposed device as assembled and ready for use. The upper body of E3 is labeled E3A, and has an upper port D1 and side valveport D3. An accordion shafted duckbill valve F is positioned horizontally on side valveport D3. As in embodiment E2, stylet A enters upper port D1 through elastomer cap D2a. In embodiment E3 stylet A is slidably and sealably surrounded by catheter L as in embodiments E1 and E2, and catheter L is connected to discoid base J and lumenized dome H as it is in embodiments E1 and E2. The sharp tip C of stylet A protrudes through distal catheter orifice M1 as in embodiments E1 and E2. As in embodiments E1 and E2, fenestrations K (not shown in FIG. 8) of base J are employed in attaching the device to patient's skin as shown in FIG. 12. A tethered elastomer cap D2a precludes outside air entry after the stylet is removed, and the cap is twistably removable to permit an airtight connection with a syringe or suction device for fluid removal via the Luer Lok fitting on upper port D1 (not shown). Upper body E3A is integral with catheter L, dome H, and discoid base J in one molded piece, making E3 a simpler design than E2. E3 is a simpler design than E2 also because E3 lacks a stopcock. The process of pneumothorax evacuation with E3 remains simple and straightforward as with other embodiments. A Luer Lok compatible syringe is enclosed within the E3 packaging, as it is with all embodiments, to allow attachment of the syringe or other suction device in case hemothorax or pleural effusion are suspected or encountered.

Figure 8A:
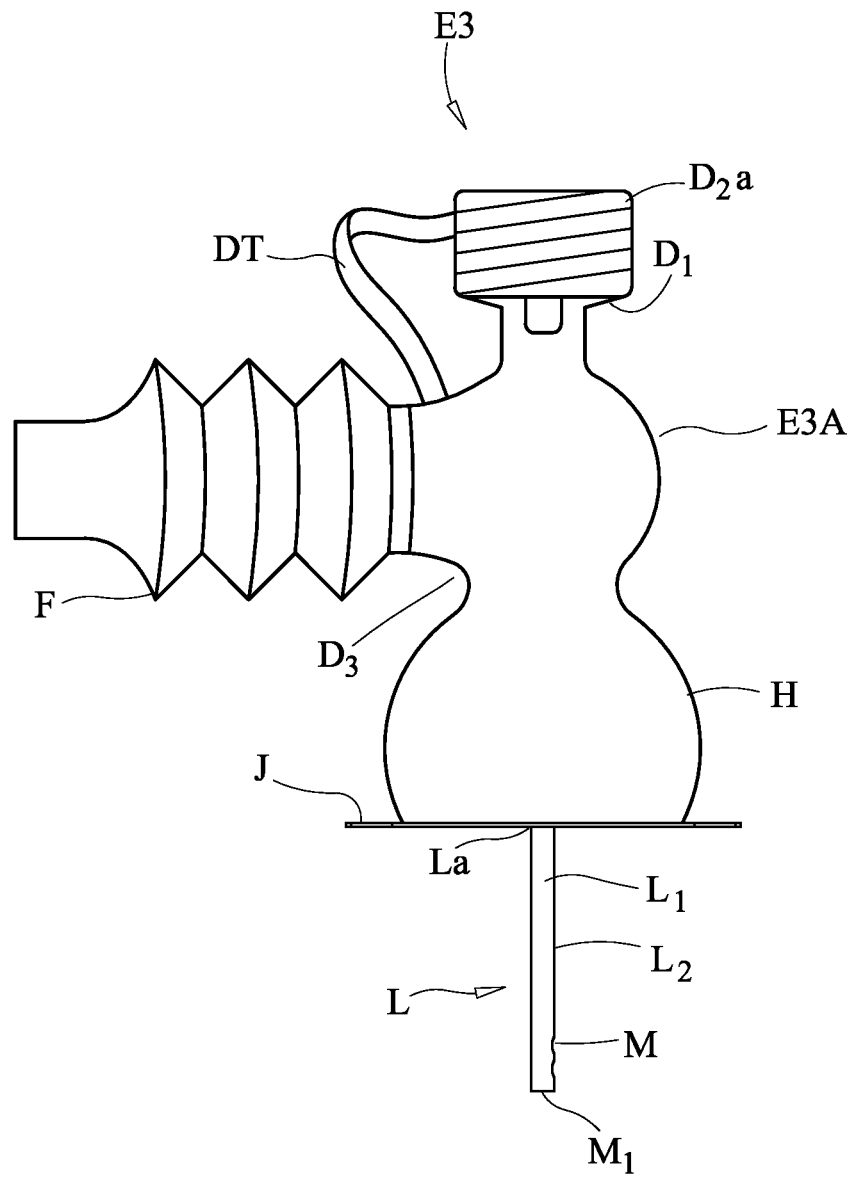
FIG. 8a is an isometric view of E3 with the stylet removed.

FIG. 8a shows embodiment E3 with the stylet removed.

Figure 9:
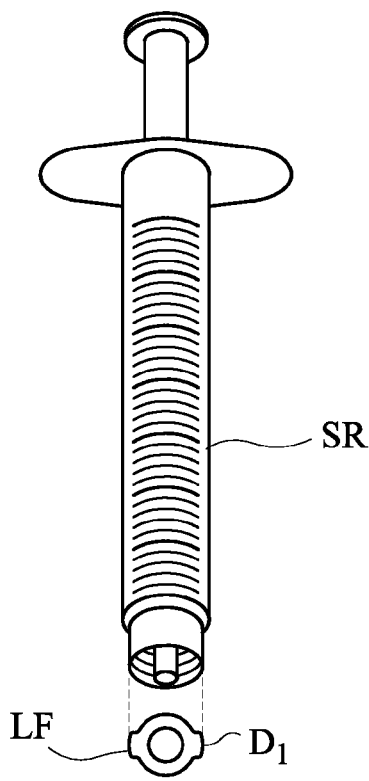
FIG. 9 is an exploded view of an upper port Luer Lok compatible fitting in accordance with embodiments of the present invention.

FIG. 9 is an exploded view of an upper port D1 with its Luer Lok compatible fitting LF for fluid suction, in all embodiments. The Luer Lok fitting LF enables the connection of the pneumothorax device to a syringe SR or other suction device in the event of pleural effusion or hemothorax. This connection is enabled by the removal of tethered twistoff elastomer cap D2a in embodiments E2 and E3. In embodiment E1, no cap is necessary, as the upper port D1 resides atop a clear sleeve G which surrounds duckbill valve F, which is positioned vertically atop said dome and within said sleeve to prevent ingress of air after the stylet is removed.

Figure 10:
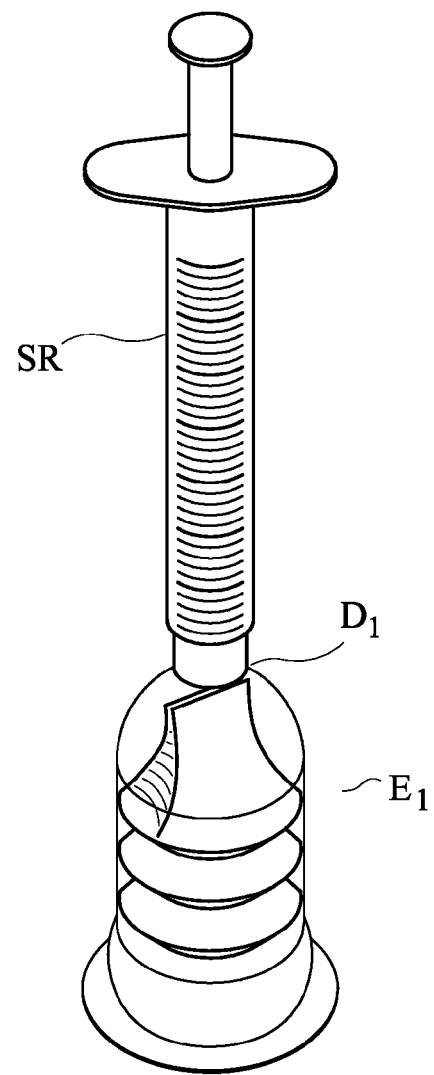
FIG. 10 is an exploded view of a device in accordance with embodiments of the present invention, showing an upper port with Luer Lok fitting connected to a syringe for fluid suction.

FIG. 10 shows the upper port in embodiment E1 in immediate connection with a Luer Lok syringe SR in the event of an identified need for suction and drainage of pleural effusion or hemothorax. In embodiment E1, upper port D1 requires no capping since valve F is contained within sleeve G, said valve remaining closed after stylet removal thereby precluding outside air entry. By way of comparison, embodiment E2 utilizes a three way stopcock D3b, wherein the upper port D1 is covered with elastomer cap D2a. This configuration permits airtight entry of said stylet and prohibits outside air entry upon removal of stylet A, but cap D2a is twistably removable to permit fluid suction.

Figure 11:
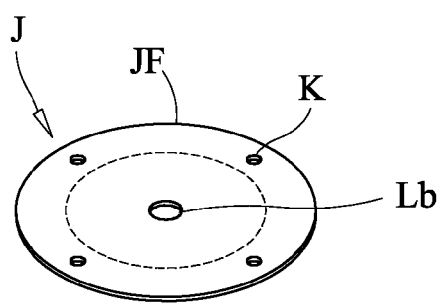
FIG. 11 is an exploded view of a discoid base in accordance with embodiments of the present invention, showing its peripheral fenestrations.

FIG. 11 is a view of discoid base J component of all three embodiments. Discoid base J has an outer ring JF that extends beyond the intersection of the discoid base and dome H (shown as a dotted line). This outer ring JF is perforated marginally with peripheral fenestrations K (in this embodiment, four fenestrations), allowing for the secure fixation of the device to the chest wall after radiographic placement has been verified. The discoid base J is comprised of the same material as dome H and catheter L. These three components may be cast in one piece, thereby minimizing the risk of mechanical separation of these components. The discoid base is contiguous with the dome, said disc lumenized in the center at the point of its attachment to the proximal end of said catheter, said lumen Lb continuous through said disc and dome for the purpose of conducting trapped air and fluid from patient's intrapleural space. The inferior surface (opposite the dome) of said discoid base J is intended to be contiguous with the skin of said chest wall, thereby permitting secure fixation to the skin of said chest wall with interrupted cutaneous sutures.

FIG. 12 shows the discoid base of FIG. 11 with sutures. Interrupted sutures Su through fenestrations K provide secure attachment of the discoid base J to the chest wall, precluding inadvertent dislodging of the catheter from the intrapleural space during patient transport as well as during routine nursing management and spontaneous patient movement. Such suturing can be accomplished readily once catheter placement has been verified, and requires no summoning of suture materials as they are packaged together with the pneumothorax device. Sutured attachment is far superior to reliance on pads treated with adhesives which are more vulnerable than sutures to loosening and separation during handling during patient transport and upon contact with moisture. Sutures are quickly removable when it is deemed safe to remove the pneumothorax device, whereupon no significant cutaneous damage results. One may opt for manual application of adhesive such as benzoin under the peripheral margin of said discoid base to hold the device long enough to verify proper placement, albeit less secure than sutures. However, adhesive application would seldom be indicated since proper placement would instantaneously be evidenced by the sudden expulsion of air via the one-way valve which would be accompanied by reduction in tachypnea, improvement in breath sounds, lessening of cyanosis, improvement in oxygen saturation, and an overall diminution in respiratory distress. Such dramatic relief can be achieved in seconds, obviating the need for temporary adhesives, thereby justifying secure placement with interrupted sutures once proper placement is evident. Moreover, four sutures properly placed peripherally through the fenestrations of said discoid base at the 3 o'clock, 6 o'clock, 9 o'clock, and 12 o'clock positions will prevent wobbling or dislodgement in four planes, as contrasted with lateral adhesive pads that would not preclude fore and aft movement.

Figure 13:
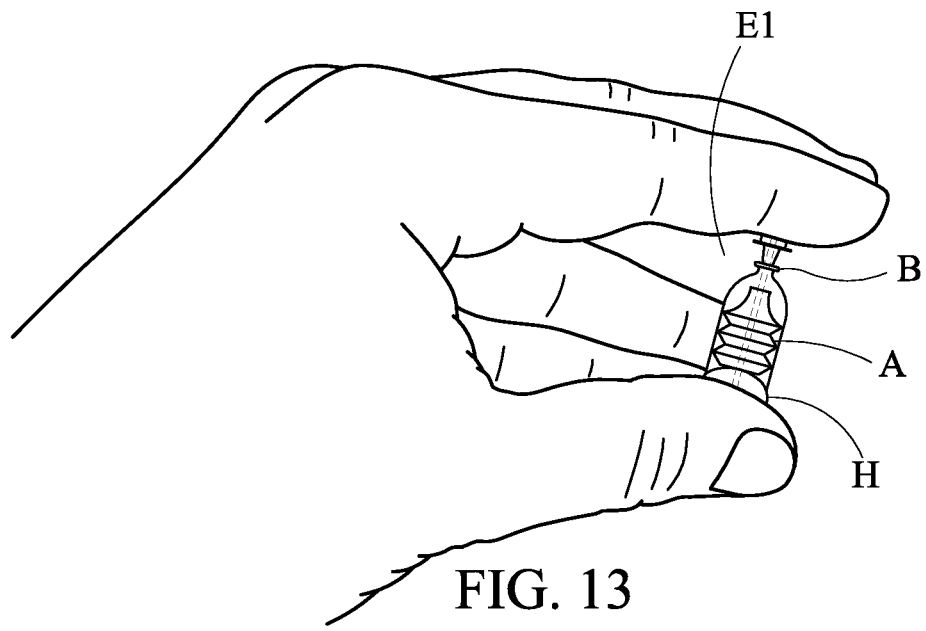
FIG. 13 depicts a technique for one-handed application of the device to the chest wall in accordance with embodiments of the present invention, showing a thumb grasping one side of a dome, 4th & 5th fingers grasping the opposite side of the dome, 2nd & 3rd fingertips atop stylet hub.

FIG. 13 shows a hand positioned for installation of a pneumothorax device, in this instance embodiment E1 of the present invention. Installation of the device can be readily achieved with one hand, with the operator placing his or her thumb on one side of dome H, his or her 4th and 5th fingertips on the opposite side of dome H, and 2nd and 3rd fingertips atop stylet hub B, then directing the device so that its stylet tip C (which is behind the operator's thumb) penetrates the intercostal space of patient's chest wall at right angles to the skin, thereby allowing entry of catheter L into the patient's intrapleural space, after which stylet A is removed to allow the evacuation of trapped air or fluid. While embodiment E1 is shown in this figure, the technique is the same for embodiments E2 and E3. As noted, proper procedure calls for sterile gloving prior to installation. Bare hands are depicted for demonstrative purposes only.

Figure 14:
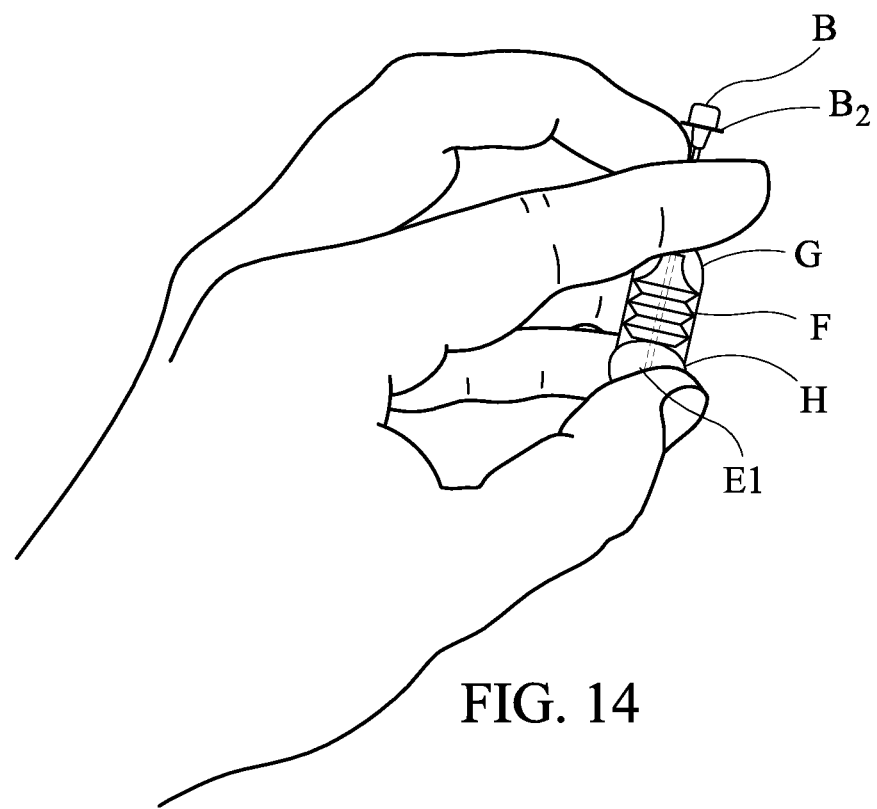
FIG. 14 depicts a technique for removal of a stylet subsequent to a successful installation of the device through the chest wall in accordance with embodiments of the present invention, with 2nd & 3rd fingertips under the annulus of stylet hub.

FIG. 14 shows the operation of removal of the stylet A using embodiment E1 of a device of the present invention. The removal of stylet A may be accomplished with the 2nd and 3rd fingertips of one hand under annulus B2 of stylet hub B, after successful placement of the device in the intrapleural space. Once intrapleural entry has been achieved, said stylet can be readily extracted, leaving catheter L (behind the operator's thumb) within the intrapleural space, thereby allowing trapped intrapleural air to escape via sidewall orifices M and end orifice M1 of said catheter, the air conducted by said catheter through said lumenized dome to one-way valve F for evacuation (see FIG. 1). Pleural effusion or hemothorax likewise are evacuated via said orifices and said catheter, by virtue of mechanical suction applied by syringe or other suction device connected to said upper port as shown in FIG. 10. While embodiment E1 is shown in this figure, the procedure for removal of the stylet is the same for embodiments E2 and E3.

Embodiments of the proposed device comprise a means for effectively treating neonatal infants and other patients who are suffering from pneumothorax, tension pneumothorax, pleural effusion, or hemothorax. The device is unique in that its discoid base, lumenized dome, and catheter are of one-piece design, is of sufficient ergonomics and compactness to readily permit one-handed installation through the chest wall, is small enough to be portable in quantity and easily stored with minimal space requirements, utilizes a small bore stainless steel stylet to minimize trauma, and has a user-friendly design favoring effective use by first responders in a neonatal emergency.

The proposed device as exemplified by its embodiments constitutes a step forward in the design and execution of devices intended for the relief of neonatal pneumothorax, tension pneumothorax, pleural effusion, and hemothorax. As noted, its small size and compactness facilitate transportability, storage, and one-hand installation. The unified molding of major components favors solidarity and resistance to separation or breakage, the simplicity of installation permits use by personnel of limited training and experience, its inherent versatility allows its legitimate use in not only the evacuation of extrapulmonic intrapleural air but also fluid and blood, and its use of inexpensive materials favors availability and economy.

While various embodiments have been described, it will be apparent to those of ordinary skill in the art that many more embodiments and implementations are possible within the scope of the invention. Accordingly, the invention is not to be restricted except in light of the attached claims and their equivalents.

GLOSSARY OF TERMS annulus: A ring, or ringlike structure.

anterior axillary line: The vertical-linear position that coincides with the forwardmost part of the axilla, or armpit. In other words, the insertion of a device in the anterior axillary line would be along the lateral aspect of the chest wall, on the up-and-down axis aligned with the front of the armpit.

auscultation: Listening to heart and lungs with a stethoscope.

barotrauma: Damage imparted by positive pressure respiration, specifically lung damage potentially caused by overly exuberant resuscitative bagging or artificial ventilation.

catheter: A tube, usually of medical plastic, used for conducting therapeutic drugs into a body compartment, or conducting air or fluid out of a body compartment.

coapt: Join together, for example in the manner of bringing together the lips, suturing together two wound edges, or the natural falling together of resilient valve lips when at rest.

contralateral: On the opposite side. For example, the spleen is normally contralateral to the appendix.

costophrenic: Of or pertaining to ribs and diaphragm. For example, as visualized on a chest Xray, the costophrenic angle is the angle made by the rib cage in relation to the diaphragm, and may be obliterated by fluid imparted by such abnormal processes as pneumonia with pleural effusion.

cutaneous: Of or pertaining to the skin.

cyanosis: Bluish discoloration, for example as seen in nailbeds and around the mouth as reflection of poor oxygenation.

distal: Further away from one's reference point. The opposite of proximal. For instance, the distal extremity corresponds to fingers and toes (rather than hips & shoulders).

effusion: A collection of fluid within a body space. For instance, a synovial effusion is an outpouring of synovial fluid within an inflamed joint. Pleural effusion is a collection of fluid within the pleural space, which is the potential space just outside the lung.

elective: Voluntary, rather than mandatory. For instance, elective cesarian section may be requested by the patient, rather than militated by an emergency.

extrapulmonic: Outside the lung.

fenestration: Opening, or window. For example, a fenestration on an implantable surgical device is an opening which might allow fixation by suturing.

hemothorax: Collection of blood within the chest. For example, severe chest wall trauma may result in a hemothorax, or bloody collection within a chest compartment such as the pleural space.

homolateral: On the same side (as). The opposite of contralateral. For example, the heart is normally homolateral to the spleen.

iatrogenic: Of or pertaining to events or effects resulting from actions of the treating physician, usually inadvertent. For example, iatrogenic pneumothorax would be pneumothorax unintentionally caused or occasioned by procedures performed by the patient's physician.

intrapleural: Within the pleural space, or between the linings of lung and chest wall (normally only a potential space).

lucency: Quality of being clear. As applied to radiology, areas of lucency appear black, or nondense, on an unenhanced Xray.

lumen: A normally patent canal. For example, a vascular lumen is the central opening in a blood vessel; a catheter lumen is the central opening down the middle of a catheter.

meconium: Fetal excrement often present in the amniotic fluid during emergency deliveries characterized by fetal distress, usually of thick sticky consistency, and capable of producing or aggravating respiratory distress if aspirated.

mediastinal: Of or pertaining to mid-thoracic viscera between the lungs, for example the heart, great vessels, and thymus gland.

midclavicular: The vertical-linear position coinciding with the mid-point of the clavicle, or collarbone. For example, insertion of a device in the midclavicular line would be placement in the up-and-down axis corresponding to the middle of the clavicle on that particular side of the body.

orifice: Opening. This could be an opening in the body, for example the mouth or anus. An orifice may be placed by design in an implantable device, as along a catheter wall to enhance drainage.

oximetry: Measurement of oxygen saturation by a device with a platinum electrode.

parenchymal, parenchymovascular: The term "parenchymal" pertains to the tissue within a solid organ. For example, parenchymal renal disease is a disease process within the tissue of the kidney, rather than the collecting system. The term "parenchymovascular" refers to the combined consideration of organ and blood vessels. For example, radiographically the pulmonary parenchymovascular markings refer to those markings on an Xray imparted by lung tissue as well as blood vessels within the lung.

parenteral: Taken into the body by a route other than via the GI tract. For example, intravenous medication is parenteral.

pleura: Epithelial lining of lung and chest wall. For example, visceral pleura is the outer lining of the lung, parietal pleura is the inner lining of the chest wall, and together they constitute the margins of the (potential) pleural space.

pneumothorax: An unnatural collection of air within the pleural space, often the result of trauma, resuscitation, or respiratory distress.

proximal: Closer to one's reference point. The opposite of distal. For example, the proximal upper extremity corresponds to the humerus (rather than the digits).

radiopaque: The quality of appearing radiodense, or white on an Xray. For example, radiopaque dyes are used in radiology to identify gastric ulcers during an upper GI contrast study.

stylet: A sharp-pointed thin instrument such as a rigid wire down the lumen of a catheter to stiffen it and allow penetration.

tachypnea: Rapid breathing.

tethered: Secured by a connection to prevent separation.

transillumination: Application of a bright light source directly against a body structure, for example the head or chest, to detect translucency from abnormal air or fluid accumulation.

trocar: sharp-pointed instrument within a cannula, including larger-bore devices for penetration into a body cavity such as the abdomen to allow withdrawal of fluid.

I claim:

1. A device for pneumothorax, tension pneumothorax, pleural effusion, or hemothorax, comprising:
    (a) a catheter comprising an outer surface having continuous longitudinal ribs extending outward from the surface to render the catheter kink resistant, a proximal opening and distal opening, said distal opening being capable of receiving gases and fluids from an interpleural space;
    (b) a rigid body comprising a flat discoid surface surrounding the lower port, and a dome intersecting the flat discoid surface, comprising a lower port on the discoid surface that is connected to and opens to the proximal opening of the catheter, a side port, and an upper port aligned with the lower port, said body having a width such that the body may be gripped with two fingers of an operator's hand, wherein the dome, discoid surface and catheter are portions of one molded piece of material and wherein the discoid surface comprises an outer ring extending outside the intersection of the dome and discoid surface, and wherein said outer ring comprises a plurality of fenestrations that allow the discoid surface to be sutured to the patient;
    (c) a one-way valve in communication with the side port of the body, said one-way valve configured to allow egress of gases and fluids from the side port and prevent ingress of gases to the side port; and
    (d) a removable stylet of approximately 18 gauge having a sharp point and a shaft that extends from the upper port, through the lower port, and through the catheter, the sharp point extending a distance past the distal opening of the catheter, wherein the stylet passes through the rigid body without passing through the one-way valve;
    (e) a hub disposed on the stylet and seated near the upper port, the hub having a hub annulus,
    wherein the body has a width and a height suitable such that the device may be gripped with two fingers of one hand on the body and another one or two fingers of the same hand on the hub to penetrate the sharp pointed instrument through a chest wall into the interpleural space, and the body has a width and a height suitable such that the hub annulus may be raised with the one or two fingers on the hub to remove the stylet while continuing to grip the body with two fingers of the same hand.

2. The device according to claim 1, wherein the one-way valve is a duckbill valve having a open end in communication with the side port and a closable end, that opens in response to pressure from the open end to allow egress of gases entering through the open end without allowing gases to enter through the closable end.

3. The device according to claim 1, wherein the discoid surface, dome, and catheter are formed of a radiopaque material.

4. The device according to claim 1, wherein the one-way valve is configured to allow egress of gases from the lower port through the side port and out of the device and prevent ingress of gases into the device through the side port.

5. The device according to claim 4, further comprising an elastomer cap disposed on the upper port that sealingly accommodates the stylet, the elastomer cap preventing ingress or egress of gases, and wherein the elastomer cap may be detached and replaced with a syringe or suction device after the sharp-pointed instrument is removed.

6. The device according to claim 4, further comprising a three-way stopcock that separates the upper port, lower port, and side port of the body.

7. The device according to claim 6, wherein the stopcock has three alternate positions, the first position allowing communication between the upper port, lower port, and side port, and which accommodates the shaft of the sharp-pointed instrument, the second position allowing communication between the lower port and side port only so that a syringe or suction device may be attached to the upper port without allowing ingress of gases and fluids, and a third position allowing communication only from the lower port to the upper port to allow removal of gases and fluids through a syringe or suction device.

8. The device according to claim 1, wherein the upper port is capable of connecting with a Luer-lok syringe or suction device for the removal of liquids.

9. The device according to claim 1, wherein the catheter has a length suitable for penetration of the chest cavity of a neonate.

10. The device according to claim 1, wherein the catheter has one or more apertures along the length of the catheter.

11. The device according to claim 1, wherein the stylet is an eighteen gauge stylet having a solid bore.

12. The device according to claim 1, further comprising a port attached to the body that allows a syringe or suction device to be attached and remove fluid received from the catheter.

13. The device according to claim 1, wherein the body of the device is less than five centimeters in width.

14. The device according to claim 1, wherein gases and fluids from the intrapleural space are released through the one-way valve immediately after the stylet is removed.

* * * * *